(12) United States Patent
DiCesare

(10) Patent No.: US 7,422,855 B2
(45) Date of Patent: Sep. 9, 2008

(54) MULTIPLEXING ASSAYS FOR ANALYTE DETECTION

(75) Inventor: Joseph L. DiCesare, Redding, CT (US)

(73) Assignee: PerkinElmer LAS, Inc., Boston, MA (US)

( * ) Notice: Subject to any disclaimer, the term of this patent is extended or adjusted under 35 U.S.C. 154(b) by 63 days.

(21) Appl. No.: 11/150,492

(22) Filed: Jun. 10, 2005

(65) Prior Publication Data

US 2006/0003366 A1    Jan. 5, 2006

Related U.S. Application Data

(60) Provisional application No. 60/521,647, filed on Jun. 10, 2004.

(51) Int. Cl.
*C12Q 1/68* (2006.01)
*G01N 33/53* (2006.01)
*C07K 17/00* (2006.01)

(52) U.S. Cl. .............................. 435/6; 435/7.1; 530/300
(58) Field of Classification Search ........................ None
See application file for complete search history.

(56) References Cited

U.S. PATENT DOCUMENTS

| | | | |
|---|---|---|---|
| 5,708,153 | A | 1/1998 | Dower et al. |
| 5,723,598 | A | 3/1998 | Lerner et al. |
| 6,027,890 | A | 2/2000 | Ness et al. |
| 6,340,588 | B1 | 1/2002 | Nova et al. ............... 435/287.1 |
| 6,387,623 | B1 | 5/2002 | Mandecki ...................... 435/6 |
| 6,534,273 | B2 * | 3/2003 | Weisburg et al. ............... 435/6 |
| 6,607,878 | B2 | 8/2003 | Sorge ............................. 435/6 |
| 6,649,351 | B2 | 11/2003 | Matray et al. ................... 435/6 |
| 6,649,414 | B1 | 11/2003 | Chandler et al. .............. 436/63 |
| 6,680,211 | B2 | 1/2004 | Barbera-Guillem et al. . 436/533 |
| 6,824,981 | B2 | 11/2004 | Chait et al. ..................... 435/6 |
| 6,858,394 | B1 | 2/2005 | Chee et al. .................... 435/7.1 |

FOREIGN PATENT DOCUMENTS

| | | |
|---|---|---|
| WO | WO99/45149 | 9/1999 |
| WO | WO02/074929 | 9/2002 |
| WO | WO04/074429 | 9/2004 |
| WO | WO05/003778 | 1/2005 |

OTHER PUBLICATIONS

Molecular Biology Reagents/Protocols 1992, United States Biochemical Corporation, 1991, Cleveland, Ohio, pp. 218-219.*
MacBeath et al, Science 289: 1762 (2000).*
Griffin et al., *Tibtech*, 18:77-84 (2000).
Griffin et al., *Analytical Chemistry* 72:3298-3302 (2000).
Lorthioir et al., *Analytical Chemistry* 73:963-970 (2001).
Pelech, *Curr. Pharm. Biotechnol.* 5:69-77 (2004).
Pusch et al., *Pharmacogenomics* 3:537-548 (2002).
Sauer et al., *Nucleic Acid Research* 28:e100 (2000).
Triolo et al., *Journal of Mass Spectroscopy* 36: 1249-1259 (2001).
Winograd et al., *Spectroscopy* 16:14-27 (2001).
International Search Report and the Written Opinion of the International Searching Authority issued for PCT/US05/20517, dated Feb. 16, 2007.
Brenner, Sydney and Lerner, Richard A., "Encoded Combinational Chemistry," Proc. Natl. Acad. Sci., vol. 89, Jun. 1992 (pp. 5381-5383).
Supplementary European Search Report, EP Application No. 05 78 4175, Mar. 25, 2008 (3 pages).

* cited by examiner

*Primary Examiner*—James Martinell
(74) *Attorney, Agent, or Firm*—Wilmer Cutler Pickering Hale and Dorr LLP

(57) ABSTRACT

High density multiplexing assays for proteins, nucleic acids, and other molecules are described based upon using mass spectrometry detection. A solid-state support assay format is utilized, whereby the bead carries both a coding molecule to track the sample or analyte and the molecule(s) necessary to perform an affinity-based assay. After the necessary reactions are complete, all of the components, e.g., coding molecule, binding molecule, analyte, and/or label are dissociated for analysis in a mass spectrometer. Various means of performing detection for the assays include different types of mass spectrometers with different types of sampling systems, including MALDI-TOF and ESI.

42 Claims, 7 Drawing Sheets

5A  5B

MULTIPLEXING ASSAYS FOR ANALYTE DETECTION

CROSS-REFERENCE TO RELATED APPLICATIONS

This application claims priority to U.S. provisional application Ser. No. 60/521,647, filed Jun. 10, 2004. The entire disclosure of the above application is incorporated by reference herein.

FIELD OF THE INVENTION

The invention relates generally to the preparation and analysis of multiple samples. More specifically, the invention relates to the use of coding moieties in conjunction with analytes for analyses of samples by methods such as mass spectroscopy.

BACKGROUND OF THE INVENTION

There are a number of assays and sensors for the detection of the presence and/or concentration of specific substances in fluids and gases. Many of these rely on specific ligand/antiligand reactions as the mechanism of detection. That is, pairs of substances (i.e. the binding pairs or ligand/antiligands) are known to bind to each other, while binding little or not at all to other substances. This has been the focus of a number of techniques that utilize these binding pairs for the detection of the complexes. These generally are done by labeling one component of the complex in some way, so as to make the entire complex detectable, using, for example, radioisotopes, fluorescent and other optically active molecules, enzymes, etc.

Advances in technology have provided techniques for assaying multiple analytes ("multiplexing") at the same time. Assaying of multiple analytes created a need for development of improved methods of sample and data analysis in which information about identity of each analyte is retained.

Examples of where multiplexing assays for DNA and proteins have been utilized include those for cytokines (e.g. U.S. Pat. No. 6,649,351), phosphoproteins (Pelech (2004); *Curr. Pharm. Biotechnol.* 5, 69-77), and single nucleotide polymorphisms (SNPs).

SNP genotyping using MALDI-TOF mass spectrometry is discussed by Pusch et al. (2002), *Pharmacogenomics* 3, 537-548. Most SNP assays involve identifying differences in polymorphisms by discriminating between the mass of individual nucleotides (Griffin et al. (2000), *Analytical Chemistry* 72, 3298-3302; Griffin et al. (2000), *TIBTECH*, 18, 77-84) or by using a mass/charge tag system (Sauer et al. (2000), *Nucleic Acid Research* 28, e100).

Mass spectroscopy has found applications in combinatorial chemistry as discussed, for example, by Triolo (Triolo et al. (2001), *Journal of Mass Spectroscopy* 36, 1249-1259). Analytical construct technology has been successfully applied to the single-bead analysis of a split-mix combinatorial library, using an analytical fragment highly sensitized to electrospray mass spectrometry (ESI-MS) and easily identified by isotope labeling (Lorthioir et al. (2001), *Analytical Chemistry* 73, 963-970). Spatially-resolved time-of-flight mass spectroscopy has also been discussed (Winograd et al. (2001), *Spectroscopy* 16, 14-27).

U.S. Pat. No. 6,649,414 provides a fluorescent particle including a core or carrier particle having on its surface a plurality of smaller polymeric particles or nanoparticles, which are stained with different fluorescent dyes. When excited by a light source they are capable of giving off multiple fluorescent emissions simultaneously, which is useful for multiplexed analysis of a plurality of analytes in a sample.

U.S. Pat. No. 6,680,211 provides a fluorescent microsphere comprised of a plurality of fluorescent nanocrystals embedded in a polymeric microsphere.

U.S. Pat. No. 6,387,623 provides materials and methods for identifying chemical compounds having desired binding properties towards a binding partner of pharmaceutical interest. The method employs transponders associated with the solid phase material used in the assay and a scanner to encode and decode data stored electronically on the transponder.

U.S. Pat. No. 6,858,394 relates to sensor compositions comprising a composite array of individual arrays, to allow for simultaneous processing of a number of samples.

U.S. Pat. No. 6,824,981 discloses compositions and methods for sensitive detection of one or multiple analytes. In general, the methods involve the use of special label components, referred to as reporter signals, that can be associated with, incorporated into, or otherwise linked to the analytes.

U.S. Pat. No. 6,607,878 is directed to methods and kits for creating and analyzing molecules using uniquely identifiable tags. The invention is also directed to methods and kits that use uniquely identifiable tags for sequencing DNA, for determining mutations, including substitutions, deletions, and additions, in sample genes, and monitoring mRNA populations.

U.S. Pat. No. 6,340,588 provides combinations, called matrices with memories, of matrix materials that are encoded with an optically readable code. The matrix materials are those that are used as supports in solid phase chemical and biochemical syntheses, immunoassays and hybridization reactions. The matrix materials may additionally include fluorophores or other luminescent moieties to produce luminescing matrices with memories. The memories include electronic and optical storage media and also include optical memories, such as bar codes and other machine-readable codes.

U.S. Pat. No. 6,649,351 provides a method for detecting a target analyte, by: (a) contacting one or more target analytes with a set of first and second binding reagents under conditions sufficient for binding of a target analyte with the first and second binding reagents, each of the first binding reagents containing a cleavage-inducing moiety and a target binding moiety, each of the second binding reagents containing a tagged probe having a mass modifier region attached to a target binding moiety by a cleavable linkage, the cleavable linkage being susceptible to cleavage when in proximity to an activated cleavage-inducing moiety; (b) activating the cleavage-inducing moiety to release a tag reporter, and (c) detecting a mass of the tag reporter, the mass uniquely corresponding to a known target analyte.

Multiplexing assays can be performed in numerous ways, however, most optimal analyte detection formats previously available limited the number of multiplexed assays that can be performed from a few in most cases to perhaps 50-100 in the best cases.

SUMMARY OF INVENTION

The invention provides solid support-based compositions, methods, kits, and libraries for high-density assays and detection of multiple analytes, for example proteins, nucleic acids, and other molecules.

In one aspect, the invention provides a composition comprising: a solid support; a coding moiety; and a binding moiety, wherein the coding moiety is attached to the solid support through a first linker, the binding moiety is attached to the coding moiety through a second linker, and the binding moiety is capable of specifically binding an analyte.

In one embodiment, the invention provides a composition comprising a plurality of coding moieties and a plurality of binding moieties, wherein each coding moiety is associated with a binding moiety. In one embodiment, all coding moieties are identical and all binding moieties are identical. In another embodiment, the plurality of binding moieties and the plurality of coding molecules is attached to the same solid support. In another embodiment, each unique coding moiety is associated with a unique binding moiety. In one embodiment, the solid support which comprises a chip. In another embodiment, the solid support comprises a bead. The bead has a diameter of about 1 to about 1000 microns, preferably of about 10 to about 200 microns. The loading capacity of the bead is about 1 pmol to about 2 nmols.

In one embodiment one or both of the first and the second linker is a covalent bond. In another embodiment, the first and the second linker form reversible links between one or more of the bead and the coding moiety and the binding moiety.

In another embodiment, the invention provides a composition, wherein the first linker and the second linker are independently selected from a group consisting of a covalent bond, a photolabile moiety and a chemically labile moiety. In one embodiment, the photo-labile moiety is selected from a group consisting of o-nitrobenzyl (and various derivatives such as methyl and alkoxy), 7-nitroindanyl and 2-nitrobenzhydryl esters or ethers. In one embodiment, the chemically labile moiety is a base-labile moiety or an acid-labile moiety. In one embodiment, the base-labile moiety is selected from a group consisting of n-alkylsulphonamides, 9-fluorenylmethyloxycarbonyl and oximes, the acid-labile moiety is selected from a group consisting of t-butoxycarbonyl, benzylcarbonyl and organic esters.

In another embodiment, the coding moiety consists of discrete building blocks. Each building block is independently selected from a group consisting of a nucleotide, an amino acid, and a carbohydrate. In one embodiment, the coding moiety comprises about 5-20 amino acids. In another embodiment, the coding moiety is an organic moiety. The organic moiety is selected from a combinatorial library and may be modified using a mass modifier, for example a lanthanide chelate.

In another embodiment, the binding moiety is selected from the group consisting of an antibody, an antigen, a protein, a peptide, a nucleic acid, a PNA, a carbohydrate, or a fragment thereof. The coding moiety is associated with a selected binding moiety or with a sample from a selected source.

In another aspect, the invention provides a method for sample analysis comprising the steps of: a) providing a composition comprising: a solid support; a coding moiety; and a binding moiety, wherein the coding moiety is attached to the solid support through a first linker, the binding moiety is attached to the coding moiety through a second linker, and the binding moiety is capable of specifically binding an analyte; b) contacting the composition with a sample to be tested for the absence, presence, or quantity of the analyte; c) exposing the sample-contacted composition to conditions effectuating a release of at least one of the coding moiety, the analyte and the binding moiety from the solid support; and d) subjecting at least one of the coding moiety and the analyte to spectrographic analysis.

In one embodiment, step c) comprises effectuating release of the coding moiety and the analyte. In another embodiment step d) comprises subjecting both the coding moiety and the analyte to spectrographic analysis, which may comprise mass spectroscopic analysis.

In one embodiment, the release of at least one of the coding moiety, the analyte and the binding moiey takes place in a mass spectrometer. Releasing the coding moiety or the analyte may comprise using a light source, which is a laser, for example, a MALDI laser. The light source may irradiate one bead at a time. In another embodiment, the release of at least one of the coding moiety the analyte and the binding moiety is effectuated by plasma. In another embodiment, releasing the coding moiety or the analyte comprises using a MALDI matrix solution.

In one embodiment, the spectrum of the coding moiety is used to aid in the identification of the analyte, for example quantification of the amount of analyte. In another embodiment, the coding moiety is used to identify the source of the analyte.

In one embodiment, mass spectroscopy is performed using MALDI-TOF, q-TOF, TOF-TOF, ICP, ESI, tandem, quadrupole, SIMS, or FAB mass spectroscopy.

In one embodiment, the beads are separated before the step of exposing the sample-contacted composition to conditions effectuating a release of at least one of the coding moiety, the binding moiety and the analyte from the solid support.

In one embodiment, the step of separating the beads comprises placing the beads in a micro-array of wells. In another embodiment, the step of separating the beads comprises spreading the beads on a target, e.g., a MALDI target. In one embodiment, the release step and the spectrographic analyisis step are performed on a single bead.

In another embodiment, the coding moiety is analyzed using a technique other than mass spectroscopy, for example by absorbance, fluorescence, IR spectroscopy, Raman spectroscopy, NMR spectroscopy, radioisotope detection, or radiofrequency detection.

In another aspect, the invention provides a method for measuring binding affinity of an analyte comprising: a) providing a composition comprising: a solid support; a coding moiety; a binding moiety; and a first analyte, wherein the coding moiety is attached to the solid support through a first linker, the binding moiety is attached to the coding moiety through a second linker, and the binding moiety is specifically bound to a first analyte; b) contacting the composition of step a) with a sample containing a second analyte capable of specific binding to the binding moiety, wherein at least a portion of the first analyte is displaced by the second analyte; c) exposing the sample-contacted composition to conditions effectuating release of the coding moiety and at least one of the first and the second analytes bound to the binding moiety from the solid support; d) subjecting the coding moiety and at least one of the first and the second analytes to mass spectrographic analysis.

In one embodiment, the method is a competitive immunoassay.

In another embodiment, the composition of step as) comprises a plurality of coding moieties and a plurality of binding moieties.

In one embodiment, each coding moiety is associated with a binding moiety. In another embodiment, the invention provides a method further comprising repeating steps a) to d) with a plurality of samples. In one embodiment, each sample contains a different analyte.

In another embodiment, the method further comprises the step of quantitating the amount of at least one of the first and the second analyte.

In another embodiment, the method comprises the step of determining a relative binding affinity for the binding moiety of the second analyte with respect to the first analyte. The first and/or the second analytes can be a nucleic acid.

In another aspect, the invention provides a method for measuring binding affinity of an analyte comprising: a) providing a composition comprising: a solid support; coding moiety; a binding moiety; and a first analyte, wherein the coding moiety is attached to the solid support through a first linker, the binding moiety is attached to the coding moiety through a second linker, and the binding moiety is bound to the first analyte; b) contacting the composition of step a) with a sample containing a second analyte capable of binding to the first analyte, wherein the first analyte remains bound to the binding moiety; c) exposing the sample-contacted composition to conditions effectuating release of the coding moiety and at least one of the first or the second analyte from the solid support; d) subjecting the coding moiety and at least one of the first and the second analytes to spectrographic analysis.

In one embodiment of the invention, the binding moiety is antibody, the first analyte is an antigen, and the second analyte is an antibody different from the binding moiety. In one embodiment, the second analyte is modified with a tag to facilitate detection.

In another aspect, the invention provides a kit comprising: a) a first component comprising: a solid support; and a coding moiety, wherein the coding moiety is attached to the solid support through a first linker and wherein the coding moiety comprises a reactive moiety at a location distal from the solid support; and b) instructions for reacting the reactive moiety with a binding moiety.

In one aspect the first component further comprises a second linker, the second linker attached to the coding moiety and comprising the reactive moiety.

In another aspect, the invention provides a library comprising a plurality of particles, wherein each particle comprises: a solid support; a coding moiety; and a binding moiety, wherein the coding moiety is attached to the solid support through a first linker, the binding moiety is attached to the coding moiety through a second linker, the binding moiety is capable of specifically binding an analyte, each particle having a unique coding moiety and a unique binding moiety.

In one aspect, each particle comprises a plurality of binding moieties and a plurality of coding moieties, wherein each binding moiety is associated with a coding moiety.

The foregoing and other features and advantages of the invention will be made more apparent from the description, drawings, and claims which follow.

DETAILED DESCRIPTION OF THE INVENTION

The patent, scientific and medical publications referred to herein establish knowledge that was available to those of ordinary skill in the art at the time the invention was made. The entire disclosures of the issued U.S. patents, published and pending patent applications, and other references cited herein are hereby incorporated by reference.

Multiplexing Assay Composition

A composition for use in high density multiplexing assays includes one or more constructs attached to a solid support in which both the coding moiety and the analyte are part of the same construct. The coding moiety and the analyte can be released from the solid support and detected simultaneously or separately for detection, quantitation, or identification purposes.

Figure 1:
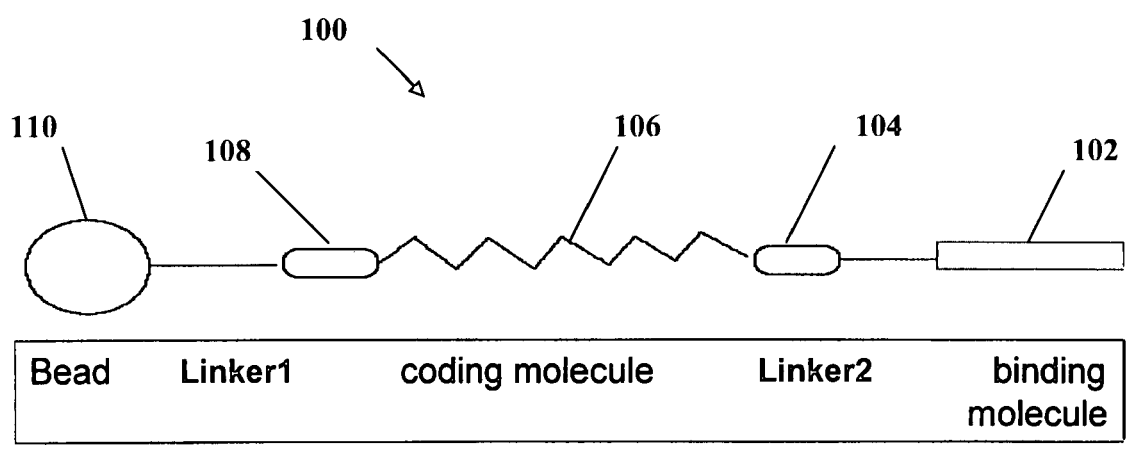
FIG. 1 is a schematic illustration of a bead-based construct including a coding moiety and a binding moiety according to one embodiment of the invention.

FIG. 1 illustrates one schematic design of the particle construct 100. In this illustrative example, a binding moiety 102 is attached to a second linker 104, which is attached to a coding moiety 106. The coding moiety is further attached to a solid support 110 through a first linker 108. An analyte can bind to the binding moiety. Other construct designs are also possible.

Solid Support

Various types of organic and inorganic types of solid supports are contemplated. The solid support may be a surface onto which multiple constructs may be linked. In one embodiment, the solid support is a bead. The composition of the solid support will vary, depending on the construct and the method of synthesis. Suitable compositions include, but are not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and Teflon may all be used. Further examples include various types of resins, e.g., polystyrene and other polymer resins, glass, gels, e.g., silica gels, alumina, silica, zeolites, and clays, e.g., montmorillonite.

Polymers suitable for use as solid supports include homopolymers or heteropolymers and may optionally be cross-linked. Exemplary polymeric materials include, but are not limited to, latex, acrylic, glass/polymer composites, thermoplastic (e.g., one or more of polystyrenes, polyvinyl chloride, polyacrylate, nylon, substituted styrsenes, polyamides, polycarbonate, polymethylacrylic acids, polyaldehydes, and the like), magnetic materials in combination with a polymeric material, and combinations thereof. Examples of cross-linked polymers include cross-linked gel type polystyrene (1-2% divinylbenzene) and poly(styrene-oxyethylene) copolymers.

Polymers can be functionalized to allow attachment of linkers, for example amines, carboxyls, sulphydryls, halides, etc., to permit wide flexibility in derivatizing to other moieties.

In another embodiment, the solid support can comprise a chip, for example a micro-chip.

In the description of the construct which follows, the solid support is referred to as a bead; however, it is recognized that the solid support may be any surface as is described herein above.

In one or more embodiments, the solid support is a bead. In some embodiments, the bead is substantially spherical, however, the bead needs not be spherical, and irregular particles may be used. Various types of porous and non-porous beads are available. In some embodiments, the beads may be porous, thus increasing the surface area of the bead available for linker attachment. Additionally, the porosity of the beads may help the efficiency of the release of the molecules form the bead, particularly in the case of a photo-labile release of molecules from the beads. If molecules are inaccessible to enough light, release may be inefficient.

The bead sizes range from nanometers, i.e. 100 nm, to millimeters, i.e. 1 mm, with beads typically ranging from about 0.2 micron to about 200 microns. As will be appreciated by those skilled in the art, the composition, shape, size, and density of the bead may vary depending on the factors such as the assay system in which it is used, as well as the nature of an analyte to be detected.

Many types of beads may be used in peptide and combinatorial chemistry synthesis reactions. Beads of various sizes and porosity have different loading capacities. The loading capacity refers to the maximum amount of a molecule that can be loaded or synthesized onto a bead. This is usually determined by the amount of the first functional group that is attached to the bead. Exemplary loading capacity is in the range of about 1 pmol to 2 nmols. For example, a common 35 micron diameter bead can have a 5.5 pmol loading capacity, while a 90 micron diameter bead can have a 90 pmol loading capacity. The loading capacity and, hence, the amount of the molecules available for release and subsequent detection are controllable bead parameters.

Typically the beads will include one or more types of reactive functionalities which react with reactive functionalities of the construct, e.g., the coding moiety, to link the construct to the beads. Exemplary reactive functionalities that may be present on the surface of the polymeric bead include carboxyl-reactive groups, a plurality of amine-reactive groups, or a combination thereof.

Coding Moieties

The beads may further include one or more molecules of a coding moiety linked to the bead through a first linker. Methods for linking the coding moieties to the surface of the beads are well known in the art. Depending on the composition of the beads, coding moieties can be selected based upon the degree of diversity required in the coding molecules, properties of the analyte, as well as on the means used for detection.

Coding moieties can be, for example, any molecules comprising discrete building blocks. Examples of building blocks include amino acids, nucleotides, carbohydrates, or organic molecules. Coding moieties can comprise different types of building blocks, each of which can independently be modified by mass modifiers or any other tags.

In one embodiment, coding moieties include, for example, polypeptides. Polypeptides can vary in length, and can be of any length. In some embodiments, polypeptides are 5-20 amino acids in length. Each amino acid can be a naturally-occurring amino acid, a D-amino acid, a non-naturally occurring, an uncommon, or a modified amino acid.

Examples of modified amino acids include, but are not limited to 2-aminoadipic acid, 3-aminoadipic acid, beta alanine, 2-aminobutyric acid, 4-aminobutyric acid, 6-aminocaproic acid, 2-aminoheptanoic acid, 2-aminoisobutyric acid, 3-aminoisobutyric acid, 2-aminopipemilic acid, 2,4-di-aminobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, sarcosine, N-methylisoleucine, 6-N-methyllysine, N-methylvaline, norvaline, norleucine, ornithine.

In another embodiment, coding molecules include nucleic acids, such as DNA, RNA, PNA. Nucleic acids can be of any length. In some embodiments, nucleic acids are 4-100 nucleotides in length. Nucleotides can be attached to each other through any hydroxyl groups in any polarity. Each nucleotide can be a deoxyribonuclotide, a ribonuclotide, a thionucleotide, a methylated nucleotide, a non-naturally occurring or a modified nucleotide.

Examples include, but are not limited to 4-acetylcytidine, 5-(carboxyhydroxymethyl)uridine, 2'-O-methylcytidine, 5-carboxymethylaminomethyl-2-thiouridine, 5-carboxymethylaminomethyluridine, dihydrouridine, 2'-O-methylpseudouridine, beta,D-galactosylqueuosine, 2'-O-methylguanosine, inosine, N6-isopentenyladenosine, 1-metyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyl-2-thiouridine, beta, D-mannosylqueosine, 5-methoxycarbonylmethyl-2-thiouridine, 5-metoxycarbonalmethyluridine, 5-methoxyuridine, 2-methylthio-N6-isopentenyladenosine, N-((9-beta-D-ribofuransyl-2-methylthiopurine-6-yl)carbamoyl)threonine, N-((9-beta-D-ribofuranosylpurine-6-yl)N-methylcarbamoyl)threonine, uridine-5-oxyacetic acid-methylester, uridine-5-oxyacetic acid, wybutoxosine, pseudouridine, queuosine, 2-thiocytidine, 5-methyl-2-thiouridine, 2-thiouridine, 4-thiouridine, 5-methyluridine, N-((9-beta-D-ribofuransylpurine-6-yl)-carbamoylthreonine, 2'-O-methyl-5-methyluridine, 2'-O-methyluridine, wybutosine, 3-(3-3-amino-3-carboxypropyl) uridine.

In another embodiment, coding molecules include carbohydrates. Examples of carbohydrates include saccharides, such as monosaccharides, disaccharides, oligosaccharides and polysaccharides. Oligosaccharides and polysaccharides can be of any length and be connected by any glycosidic linkages. Polysaccharides can be heteropolysaccharides or homopolysaccharides. Monosaccharide building blocks can be aldoses or ketoses, D or L stereoisomers, cyclic or acyclic, and may contain about 4-5 carbon atoms. Monosaccharides can be linked by alpha or beta glycosidic links, which can be 1→2, 1→3, or 1→4 glycosidic links.

The appropriate coding moiety is selected, at least in part, depending on the detection method. In some embodiments, the coding moiety has a molecular weight, for example below 1,500, is stable and readily ionizable, and is not obscured by other signals that can be observed in mass spectra, such as MALDI matrix ions. For example, peptides are a good choice for MALDI-TOF mass spectrometry detection. In some embodiments, the coding moiety contains less than 50% hydrophobic residues and no more than 5 or 6 hydrophobic residues in succession. In another example, the coding moiety can be rich in arginine for increased stability or it can contain a terminal arginine residue for increased sensitivity. In another example, the coding moiety comprises residues other than tryptophan, cysteine, methionine, glutamine and asparagines, which can be susceptible to degradation.

In other embodiments, coding molecules include organic molecules. Organic molecules may be synthesized by combinatorial methods and can be further modified, for example, by attachment of a mass tag. Small organic molecules from combinatorial libraries are suitable choices for electrospray introduction into the mass spectrometer. Various mass modifiers such as lanthanides. Lanthanide chelates, or other chelates are good choices for ICP-MS detection.

Binding Moieties

Binding moieties describe any molecule which has increased binding specificity and affinity for a an analyte or a component or a fraction thereof. Binding moieties preferably exhibit increased affinity for an analyte, and even more preferably specific binding affinity for one analyte compared to other analytes. Binding moieties are attached to the coding moieties via a second linker, preferably in a way that the affinity and specificity of the binding moiety for the analyte is not significantly altered.

Many different binding moieties are contemplated in this invention. Examples of binding moieties include antibodies, antibody fragments, antigens, peptides, proteins, nucleic acids, aptamers, carbohydrates, small molecules, coordination complexes, similar affinity-type molecules, and portions thereof. Synthetic binding moieties such as organic molecules are also contemplated. All binding moieties can be further modified if desired.

Linkers

Linkers serve to reversibly link two components of the construct, for example, the coding moiety to the bead, or the binding moiety to the coding moiety. A linker is typically a small chemical moiety that bridges the two components of the construct. The linker may be a simple covalent bond between the two components, or a chemical group containing a free reactive group that is reactive with another free reactive group. By the term "reversibly link" is meant, a bond or an association of sufficient stability to withstand conditions encountered under assay conditions, but with sufficient liability to be cleaved before or during a method of detection. As known to those skilled in the art, the reversible link may comprise one or more of hydrogen, ionic, van der Waals, covalent (for example a disulfide link) and the like. As also known to those skilled in the art, and as will be more apparent by the following embodiments, there are several methods and compositions in which two or more molecules may be reversibly linked using reactive functionalities of a linker. Reactive functionalities include, but are not limited to, free chemical groups (e.g., thiol, or carboxyl, hydroxyl, amino, amine, sulfo, etc.), and the like.

Linkers contemplated in this invention include linkers known in the art for solid state synthesis and combinatorial chemistry. Linkers include carboxylic acid linkers, carboxamide linkers, alcohol linkers, amide linkers, traceless linkers and any other appropriate linkers. In many examples, solid support, such as a resin will be pre-functionalized with one or more types of linkers. Examples of such resins include polystyrene resins, Wang resins, SASRIN resins and other resins. Polystyrene resins may be cross-linked and functionalized, for example with a haloalkyl group. In many instances, these resins will comprise beads. Conditions for cleaving these linkers include hydrogen fluoride, TFA, or any other acidic conditions.

Examples of carboxamide linkers include methylbenzhydrylamine, modified and unmodified xanthenyl groups, Rink amide linkers, and other linkers. Examples of alcohol linkers include tetrahydropyranyl-based linkers, trityl-based linkers and others. Examples of traceless linkers include, for example, silyl linkers.

Analytes

Analytes refer to a molecule of an organic or inorganic nature, the presence and/or quantity of which is being tested for, and which contains a component (domain or sequence or epitope or portion or chemical group or determinant) for which the binding moiety has binding afffinity and specificity for a component or portion of one analyte over that of a different analyte. Different binding moieties are capable of binding different analytes. Examples of suitable analytes may include, but are not limited to, a nucleic acid molecule, nucleotides, aptamers, amino acids, peptides, proteins, glyco-proteins, eukaryotic or prokaryotic cells, lipoproteins, carbohydrates, lipids, phospholipids, aminoglycans, chemical messengers, biological receptors, structural components, metabolic products, enzymes, antibodies, antigens, drugs, therapeutics, toxins, inorganic chemicals, and any other organic molecules.

Analytes are detected through their ability to specifically bind binding moieties while the binding moieties are attached to the solid support.

Larger moieties comprising one or more of these analytes are also contemplated, for example, viruses with protein receptors on their surfaces.

Synthesis of Constructs

Constructs can be synthesized directly on the solid support or synthesized first and subsequently attached to functional groups on the solid support. Principles of solid state synthesis are well known to one skilled in the art. Exemplary references include *Solid Supports and Catalysts in Organic Synthesis*; Smith, K., Ed.; Ellis Horwood and PTR Prentice Hall: New York, 1992; *Polymer-Supported Reactions in Organic Synthesis*; Hodge et al., Ed.; John Wiley & Sons: New York, 1980; *Solid-Phase Organic Synthesis*; Burgess, Ed.; Wiley-Interscience: New York, 2000; and *Solid-Phase Synthesis: a Practical Guide*; Kates et al.; Marcel Dekker, Inc.: New York, 2000.

Assays

Once the entire bead construct is assembled, reactions between beads and analytes are conducted using standard techniques known in the art, such that analytes, if present, will bind to the binding moieties. Various binding assays may be performed on the beads. An assay may be designed to detect the presence, absence, or quantity of a particular target analyte; for example, the presence, absence, or quantity of a particular nucleotide sequence or a particular protein, such as an enzyme, an antibody or an antigen. Alternatively, the assay may be designed to screen for bioactive agents, i.e. drug candidates, for binding to a particular target analyte.

Figure 2:
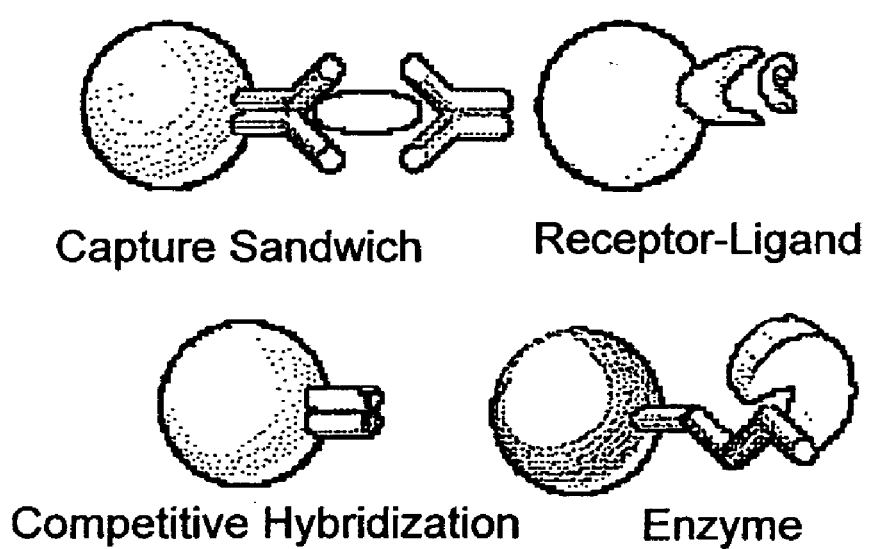
FIG. 2 is an illustration of various binding assays that may be performed on the bead-based constructs according to one embodiment of the invention, including capture sandwich, receptor-ligand, competitive hybridization and enzyme-substrate binding.

FIG. 2 illustrates the many types of binding assays that may be performed on the bead, including capture sandwich, receptor-ligand, competitive hybridization and enzyme-substrate binding. Other assays, such as a competitive binding assay may also be performed. Affinity reaction schemes not shown are also contemplated by this invention.

A capture-sandwich assay comprises using a binding moiety that binds a first analyte, which then binds a second analyte. This method may be used when it is difficult, impractical, inconvenient, or expensive to directly detect the second analyte, or when it is desirable to detect a multi-analyte complex.

In one embodiment, the capture-sandwich assays comprises an ELISA assay. In an exemplary ELISA assay, the binding moiety is a polyclonal antibody, the first analyte is an antigen, and the second analyte is a monoclonal antibody. Other combinations and permutations of antibodies, antigens, and fragments thereof may also be used. The binding moiety and analytes may further be modified as desired.

In another embodiment, the capture-sandwich assay comprises a hybridization assay. In an exemplary hybridization assay, the binding moiety is a nucleic acid, the first analyte is a nucleic acid cable of hybridizing to the binding moiety, and the second analyte is a nucleic acid capable of hybridizing to a portion of the first analyte. Preferably, the binding moiety and the second analyte hybridize to different portions of the first analyte. The second analyte may optionally be modified to facilitate detection.

In another embodiment, the capture sandwich assay or other assays may be used as tools for monitoring reaction progress and kinetics, with or without the use of a reaction quenching moiety.

A receptor-ligand assay comprises using a binding moiety, capable of specific binding to a ligand. The receptor can be, for example, a peptide, a protein, an antibody, or a nucleic acid. A ligand can be an organic molecule, a hormone, a peptide, or any other suitable ligand, including a ligand that is part of a larger moiety.

A competitive hybridization assay comprises using a nucleic acid or a modified nucleic acid as a binding moiety as well as the analyte. Because hybridization affinity of nucleic acids is sequence dependent, nucleic acid molecules with higher degree of complementarity to the binding moiety, will exhibit stronger degrees of affinity. This assay can be used to find an analyte with the highest affinity to the binding moiety from a pool of analytes. Examples of binding moieties and/or analytes include nucleic acids such as DNA, RNA, PNA, aptamers, or any modifications thereof. These binding moieties and/or analytes may be single or double stranded and include triplex and quadruplex DNA structures, DNA/RNA hybrids, ribozymes, deoxyribozymes and similar molecules. Hybridization may include Watson-Crick base-pairing, as well as Hoogsteen, reverse-Hoogsteen, and other types of non-Watson-Crick base-pairing.

In one embodiment, the competitive hybridization assay comprises either a binding moiety or an analyte, which is capable of specific recognition of DNA or RNA base-pairs or a portion thereof. Examples include minor groove binders such as distamycin, netropsin, their analogs, other polyamides, and any other naturally occurring or synthetic molecules capable of specific interaction and/or recognition of nucleic acids. These assays may be used for identification of nucleic acid binding compounds with desired binding properties, or identification of nucleic acids with desired binding properties to these compounds. Other uses are also contemplated.

An enzyme-substrate binding assay comprises using a binding moiety, capable of specific binding to an enzyme or a portion thereof. The substrate can be, for example, a peptide, a protein, a nucleic acid, a hormone, an organic molecule, or any other molecule. The enzyme can be a protein, an antibody, a nucleoprotein, a nucleic acid such as a ribozyme or deoxyribozyme. The enzyme can further be part of a larger moiety. An example of this assay is protein/nucleic acid binding assay, such as a protein/DNA binding assay.

A competitive immunoassay can be used to indirectly determine the amount of analyte present in a sample by its ability to compete with a known added quantity of the analyte. The analyte bound to the binding moiety, for example an antigen, is labeled with a mass label that does not affect its ability to bind to the binding moiety. If the sample contains a large quantity of the unlabeled analyte, then little or no labeled analyte will remain bound to the binding moiety and the measured signal will be decreased or absent. If the sample contains a small amount of analyte, then the measured signal will remain high, as little or no competition is present. This assay could also be performed with an unlabeled analyte bound to the binding moiety if the sample contains or is assayed for content of the labeled analyte. In this example, the signal would increase with the amount or concentration of the labeled analyte in the sample.

A competitive binding assay comprises using a construct in which a first analyte is attached to the binding moiety prior to the binding assay. Preferably, this first analyte has a known binding affinity for the binding moiety. The construct is then placed in contact with a sample containing a second analyte for a period of time.

In one embodiment, constructs are incubated with samples containing a second analyte for incubation periods of different lengths. After each incubation period, coding moieties and bound analytes are released from the solid support and quantitated. The amount of the coding moiety relates to the initial amount of the first analyte bound to the coding moiety. The amount of the bound first and second analytes can also be detected. From this information, kinetic information and/or relative or absolute binding affinities can be extracted using techniques and methods known in the art.

In another embodiment, constructs are incubated with samples containing different, but known, concentrations of the second analyte. After an incubation period, during which the binding is allowed to achieve equilibrium, coding moieties and bound analytes are released from the solid support and quantitated. The amount of the coding moiety relates to the initial amount of the first analyte bound to the coding moiety. The amount of the bound first and second analytes can also be detected. From this information, kinetic information and/or relative or absolute binding affinities can be extracted using techniques and methods known in the art.

A primer extension assay comprises using a polymerase enzyme to incorporate one or more nucleotides into a nucleic acid strand. For example, the binding moiety can comprise a nucleic acid template, for example a DNA or an RNA molecule. The analyte, for example, can be the nucleic acid, which is a product of a primer extension reaction. This analyte can be a DNA, an RNA, or any other nucleic acid molecule comprising ribonuclotides, deoxyribonucleotides, and/or other nucleotides, each of which can optionally be modified.

In some instances, at least one of the nucleotides to be incorporated is a dideoxy nucleotide. One of the possible applications of this type is determination of nucleic acid variants, particularly those containing a single nucleotide change, commonly referred to as a SNPs (single nucleotide polymorphisms). These types of assays may be performed along with an amplification and/or so-called extension assay (or specific cleavage assay).

Figure 3:
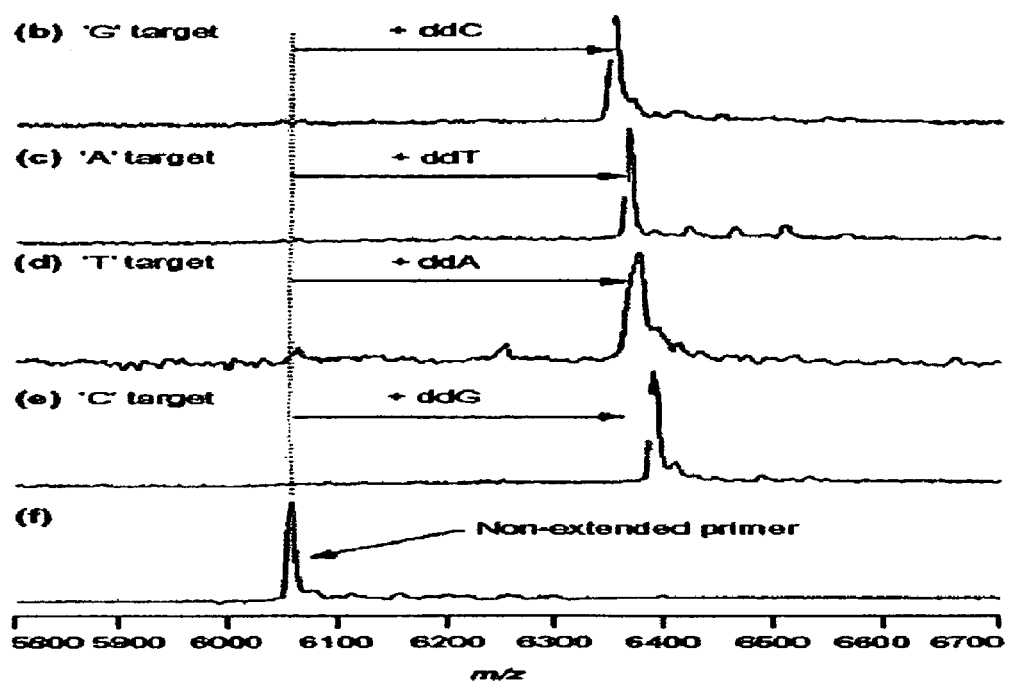
FIG. 3 illustrates mass spectra of four possible extension products from a oligonucleotide primer extension reaction generated using MALDI-TOF mas spectroscopy.

For example, in order to determine which of the four bases occurs at a specific site, a primer can be extended by one base in the presence of terminating dideoxy nucleotides. Only the specific complementary base will be incorporated as an extension to the primer and the extension reaction terminates. The dideoxy nucleotide incorporated can then be ascertained by determining the mass of the extended primer. Using high resolution MALDI-TOF mass spectrometers, extension products with molecular weights from about 3,000 to about 10,000 can be resolved. FIG. 3 provides an example of how the reaction product is detected using MALDI-TOF mass spectrometry. A primer having a mass of approximately 6,050 is extended by a single base and the mass spectra of the four possible resulting extension products is shown. From the mass difference between the primer and the extension product, the identity of the incorporated base can be determined.

Other primer extension-based methods are also contemplated by this invention.

Multiplexing

Multiplexed assays can be carried out at very high densities, e.g., hundreds or thousands of assays at a time, and/or with very high sensitivity and resolution. In one embodiment, this can be facilitated using mass spectrometry detection.

Figure 4:
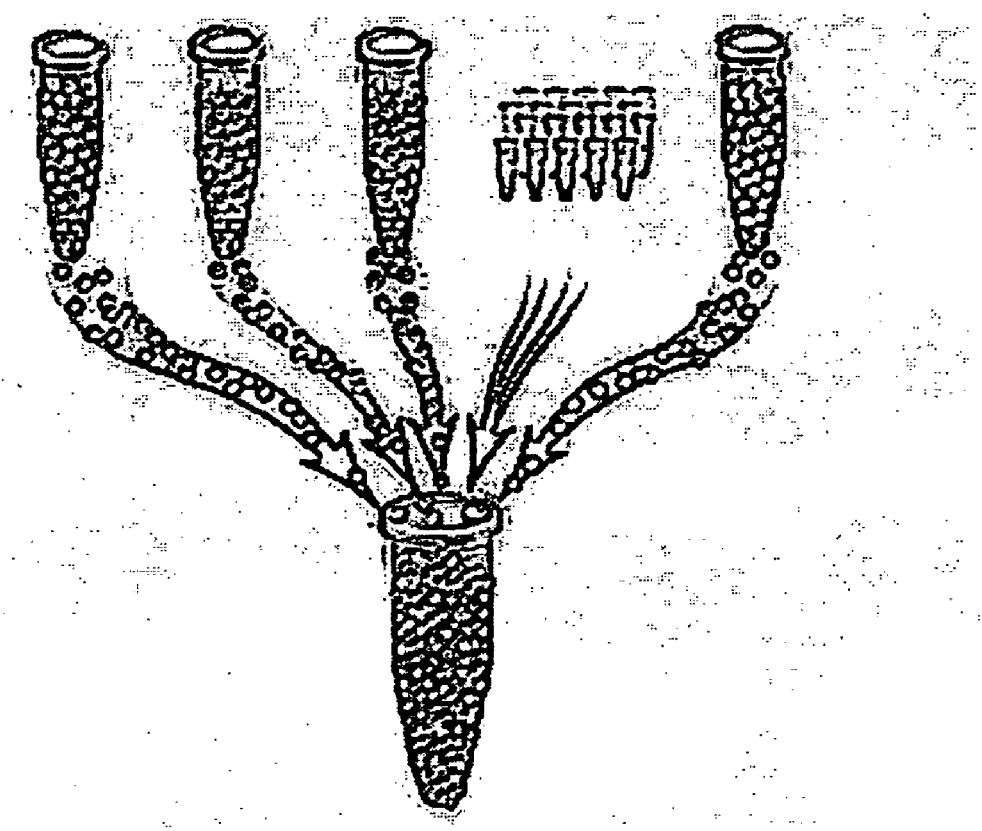
FIG. 4 depicts the general multiplexing scheme using a bead-based assay system.

FIG. 4 depicts a general multiplexing scheme using a bead-based assay system. The beads are encoded so that individual beads can be assayed and a determination made as to their content. Beads containing different coding moieties and different binding moieties and/or analytes can be pooled and analyzed together. Alternatively, beads containing different binding moieties are mixed together and reacted with analytes in a common reaction vessel (microplate well, tube, etc.).

In one instance, the measurement platform is based upon a bead-bound reaction and separation scheme. A single bead defines a single assay, although multiple beads containing the same binding moiety will allow for replicate measurements.

In one embodiment of the invention, large numbers of target analytes are assayed in a parallel fashion. In another embodiment, many samples are assayed for a single analyte using this approach.

Solid Support Separation

After reactions between analytes and the bead-bound binding moieties are complete, the particles are analyzed. In one embodiment, the particles are analyzed individually, which necessitates separation of particles. Various methods of bead separation may be employed.

Figure 5:
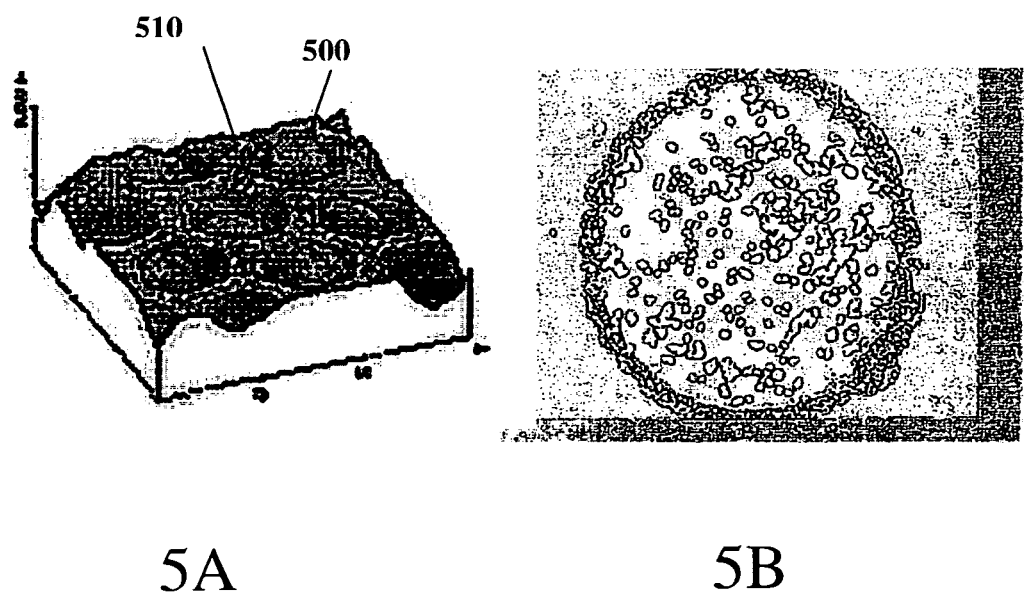
FIG. 5A is a perspective illustration of a microarray of wells for capturing and isolating individual beads in each well.
FIG. 5B is a photomicrograph of a typical MALDI target containing MALDI matrix crystals on the order of 10-50 μm in size.

After reactions are completed, beads can be separated in various types of arrays. One example is a microarray of wells that can be slightly larger than the individual beads, an example of which is shown in FIG. 5A. Beads are forced into the wells by various physical means, for example, by centrifiguation. FIG. 5A shows beads 500 on the order of 5 μm captured in wells 510 that in this instance are slightly larger in diameter. Another exemplary means of separation is simply to spread the beads on a MALDI target. FIG. 5B shows a picture of a MALDI target containing matrix crystals approximately the size of beads (about 10-50 μm).

In both of these cases, the individual beads can be detected optically and analyzed by interaction with an appropriate MALDI laser source. Since MALDI-TOF instruments include a light source and camera to aim the laser, this mechanism can also be used to locate individual beads, whether located in a microarray well or absorbed onto a MALDI target. Single beads can be analyzed by focusing the laser beam directly onto each bead.

Another exemplary means of separation is to aspirate a bead solution into a capillary having a diameter only slightly greater than the diameter of the beads, so that beads flow in single file through the capillary. Beads can then be analyzed individually as they emerge from the capillary.

In an example when an electrospray ion source is used, beads can be aspirated into a flow stream of appropriate dimensions such that beads are aligned in single file such as in a flow cytometer. Alternatively, many other schemes to capture individual beads are available.

In the example of ICP-MS format, the components are introduced into the mass spectrometer via a flowing stream.

Release of Moieties From the Solid Support

As depicted in FIG. 1, the coding moiety is linked to the bead at one end by a first linker and to the binding moiety at the other end by a second linker. In many instances, prior to analysis of the coding moiety and the analyte, both need to be released from the solid support. Thus, at least one of the first and second linker is labile, that is, the link between the construct components may be cleaved under conditions that do not negatively affect the components of the construct that are to be detected and/or analyzed. Examples of labile linkers include photo, acid or base labile linkers.

Figure 6:
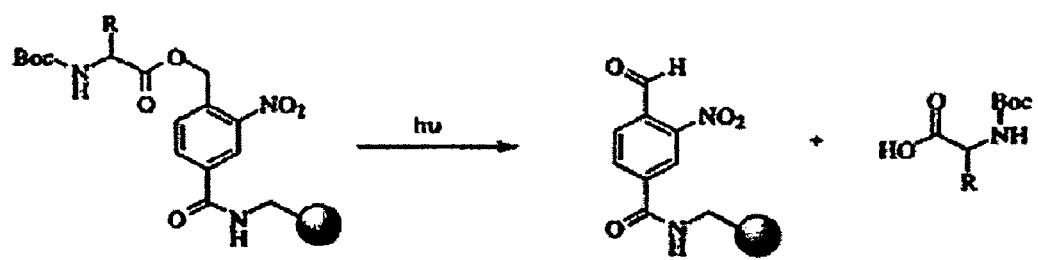
FIG. 6 illustrates a reaction scheme for the photo-induced release of a bead-bound amino acid.

Photolabile linkers are cleaved by photolysis, which can be achieved using a light source. In one embodiment, this light source is a laser. If the laser is a MALDI laser, it can be used to facilitate photolysis and ionization simultaneously. Other light sources may also be used to bring about photolysis of the photolabile linkers. Exemplary photolabile linkers are 4-[4-(1-aminoethyl)-2-methoxy-5-nitrophenoxy] butanoic acid, o-nitrobenzyl (and various derivatives such as methyl and alkoxy), 7-nitroindanyl and 2-nitrobenzhydryl esters or ethers. FIG. 6 illustrates the release of a bead-bound amino acid from a bead using photolysis. The photolabile linker is an o-nitrobenyl moiety that is linked to the bead through an amide bond and to the peptide through an ester bond. Upon irradiation with light of the appropriate wavelength, the photolabile linker is cleaved at the ester bond to release a free amino acid. Note that in this example, the linker remained on the bead. In other embodiments, a portion of the linker may be released with the construct component.

Figure 7:
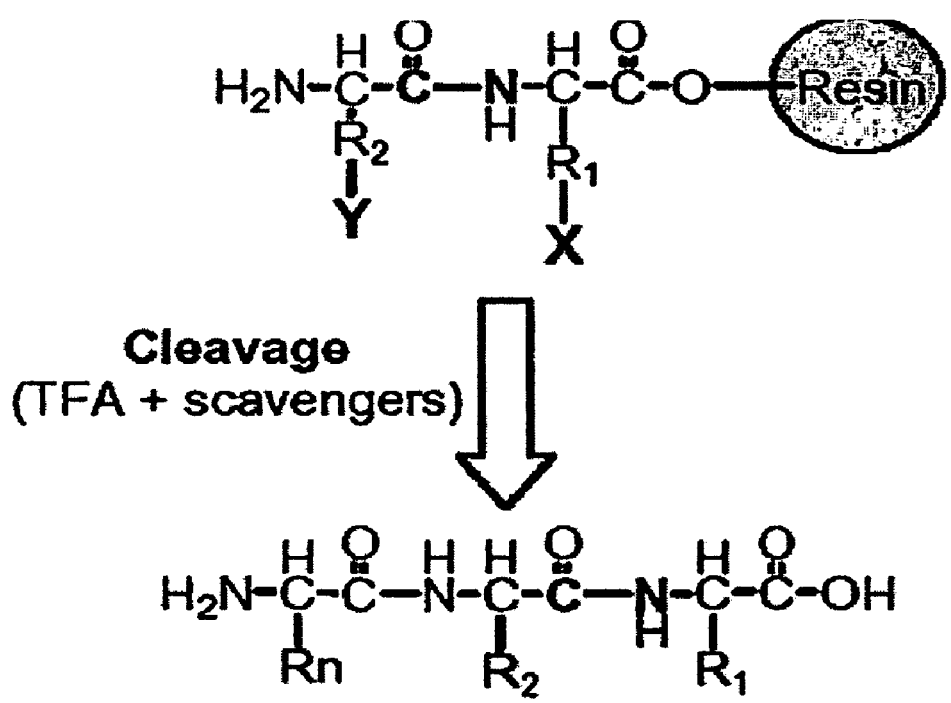
FIG. 7 illustrates a reaction scheme for the acid-induced release of a bead-bound peptide.

Chemically labile linkers, such as acid labile and base labile linkers, are cleaved by various chemical means, for example by acid or base hydrolysis. Exemplary acid-labile moieties include t-butoxycarbonyl, benzylcarbonyl and other organic esters. Exemplary base-labile moieties include n-alkylsulphonamides, 9-fluorenylmethyloxycarbonyl and oximes. An example of chemical cleavage is shown in FIG. 7 for the cleavage of a bead bound-peptide by trifluoracetic acid (TFA). Note that in this case the linker between the bead and the peptide is simply a covalent bond between the bead resin and the carboxyl group of the peptide. Thus the linker need not include additional atoms but need only to provide a reversible link between the components of the construct. Similarly, bead-bound peptides may be released by treatment with bases, such as sodium hydroxide.

If upon the release of the coding moiety from the solid support, the coding moiety is chemically modified by the hydrolysis or photolysis of the linker, this difference in mass will be taken into account when looking for the presence of a signal of the coding moiety, for example in a mass spectrogram.

The coding moiety and/or analyte can then be ionized and analyzed in a mass spectrometer. In instances where a MALDI ionization technique is used for mass spectroscopy, the acidity of the MALDI matrix can be sufficient to effectuate cleavage of acid labile linkers.

In an example where ICP mass spectroscopy is used, the entire particle can be introduced as the plasma will release the coding and the binding moiety from the solid support. Because the inductively coupled plasma causes molecules to break down, the coding moiety and the analyte need to carry distinct elemental labels. Lanthanide chelates, for example, can be used for labeling of peptides and nucleic acids.

Detection

Various means for detection of coding moieties and analytes are contemplated by this invention. Coding moieties and analytes can be analyzed by the same or by different techniques.

In many instances, mass spectroscopy is used for detection of the coding moiety and the analyte. Mass spectrometry can be used for detection of both the coding moiety and analytes, as well as specific labels attached to either. Various mass spectrometery techniques and instruments can be used.

A MALDI-TOF, a q-TOF, TOF-TOF, mass spectrometer can be used to detect and identify both the coding moieties, the analytes, and other tags from a single bead.

Another mass spectrometry means to analyze beads is by using electrospray ionization along with a mass spectrometer. In this case various types of mass spectrometers can be used including ion traps, quadrapoles, TOF's, FTICR's and various tandem combinations.

Electrospray ionization is favored for both very large and small molecules. The electrospray process produces multiply charged analytes, making it somewhat easier to detect larger analytes such as proteins. Also, small molecules can be measured readily in the absence of matrix. The MALDI process requires a matrix, which may make it more difficult to analyze small molecules, for example, with molecular weights of less than about 700 daltons.

With certain mass spectrometers, for example, MALDI-TOF, sensitivity decreases as the molecular weight of a molecule increases. For example, the detection sensitivity of molecules with molecular weights in the range of about 10,000 daltons may be an order of magnitude or more lower than detection sensitivity of molecules with molecular weights in the range of about 1,000 daltons. Use and detection of a coding moiety and/or labels with a different, for example lower, molecular weight than the analyte can therefore enhance the sensitivity of the assay. Sensitivity can also be increased by using a coding moiety and/or that is very amenable to ionization.

In electrospray mass spectrometry, sample introduction into a mass spectrometer such as a quadropole, an ion trap, a TOF, a FTICR, or a tandem mass spectrometer, the higher molecular weight compounds, for example, proteins are observed as ions having a variable number of charge states. While the multiple charge phenomenon increases sensitivity, the spectra are more complex and difficult to interpret. Use and detection of a coding moiety with a less complex mass spectrum than the analyte can therefore enhance the resolution of the assay.

Other techniques suitable for detection, for example, absorbance, fluorescence, IR spectroscopy, Raman spectroscopy, NMR spectroscopy, radioisotope, or radiofrequency detection can also be used.

Applications

The invention relates to many different types applications, some of which have already been mentioned. The applications discussed below are only exemplary and applications are also contemplated. Many applications may benefit from the high sensitivity and dynamic range of the assays described in this invention.

Medical Applications

In one embodiment, medical applications contemplated by this invention include using coding moieties for identification of a patient associated with the an analyte or analytes. This may be advantageous in cases where sample analysis is expensive, time consuming, or difficult to obtain or perform.

In another embodiment, coding moieties are used for identification of different analyte-containing samples from the same patient, for example samples taken at different times, samples from different tissues, or pre-post treatment comparisons. This embodiment also includes comparison of sample among different patients, groups of patients, populations, or any other groups.

Drug Design And Screening

In one embodiment, the invention provides applicable to drug design and development. For example, the invention provides methods for rapid screening of a series of compounds against a target, for example a library of compounds.

In another embodiment, the invention provides methods for screening of one or more compounds against one or more targets, for example a library of targets. Use of coding moieties provides information about the compound and/or target being screened.

Research And Development

In one embodiment, the invention provides methods for performing multiplex assays, which can be used in industrial and academic research applications. Exemplary methods include screening products produced by methods comprising a pool of compounds or building blocks, such as a library or a random pool. In one embodiment, the methods of the invention can be used as a tool for selection of compounds and molecules with desirable properties. The information from the coding moiety can then be used as a feedback mechanism to improve or otherwise alter the next generation of compounds and molecules.

In another embodiment, the invention provide methods to measure binding and/or kinetic properties of molecules, which can be used as a tool for selecting and/or designing of molecules with desirable properties.

In another embodiment, the invention provide methods for studies related to protein folding and design and mutagenic analyses.

In another embodiment, the invention provide methods for studies related to reaction kinetics and mechanisms.

EXAMPLES

Example 1

Synthesis of A Bead Construct Using A Peptide As A Coding Moiety

A coding moiety containing any amino acid sequence is synthesized using conventional solid phase peptide synthesis using either the Fmoc (9-flourenylmethloxycarbonyl) or Boc (tert-butyloxycarbonyl) strategy. In either case, the peptide is synthesized on a solid support (a synthetic polymeric bead) that bears a reactive group (e.g. amino group) using a automated synthesizer instrument (e.g., Advanced ChemTech ACT496). Resins containing acid or base sensitive or photochemically sensitive linkers can be purchased from NOVAbiochem. Using the Fmoc synthesis, the first Fmoc amino acid is attached to the bead via an acid labile (e.g. trifluoroacetic acid) or other type of a linker. Then, a cyclical procedure containing a certain number of steps for each amino acid addition is followed. These steps include: Fmoc deprotection, DMF (dimethyl formamide) wash, ethanol wash, addition of activated amino acid, side chain capping, DMF wash.

To utilize photolabile linkers in the coding amino acid or PNA (see below), the linker 4-[4-(1-(Fmocamino)ethyl)-2-methoxy-5-nitrophenoxy) butanoic acid (FMNB), available from NOVAbiochem, is utilized in both the first and last positions of the amino acid sequence.

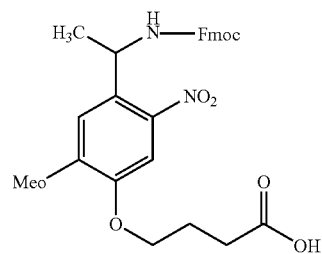

Synthesis of A Construct Containing A Peptide Coding Sequence

1. Attach FMNB photolinker to appropriate bead (e.g. Wang resin) using Fmoc synthesis chemistry;

2. Attach specific amino acid sequence (coding sequence) to photolinker utilizing cyclical Fmoc synthesis scheme as indicated above;
3. Attach FMNB photolinker to terminal position of amino acid sequence;
4. Remove protecting groups from construct, including Fmoc group on terminal photolinker unmasking free amino group;
5. Attach specific binding molecule, e.g. antibody carboxyl group, to amino group on terminal photolinker using carbodiimide chemistry (1-Ethyl-3-[3-dimethylaminopropyl] carbodiimide Hydrochloride; Pierce).

Example 2

Synthesis of A Bead Construct Using A Nucleic Acid As A Coding Moiety

Peptide Nucleic Acid (PNA) is an analogue of DNA in which the backbone is a pseudopeptide rather than a sugar. PNA mimics the behaviour of DNA and binds complementary nucleic acid strands. The neutral backbone of PNA results in stronger binding and greater specificity than normally achieved. In addition, the unique chemical, physical and biological properties of PNA have been exploited to produce powerful biomolecular tools, antisense and antigene agents, molecular probes and biosensors. New applications have emerged that could not be performed using oligonucleotides.

A coding moiety containing peptide nucleic acids (PNAs) is synthesized using a conventional solid phase synthesizer as described above.
1. Attach FMNB photolinker to appropriate bead (e.g. Wang resin) using Fmoc synthesis chemistry;
2. Attach specific PNA sequence (coding sequence) to photolinker utilizing cyclical Fmoc synthesis scheme as indicated above;
3. Attach FMNB photolinker to terminal position of PNA sequence;
4. Remove protecting groups from construct, including Fmoc group on terminal photolinker unmasking free amino group;
5. Attach specific binding molecule, e.g. antibody carboxyl group, to amino group on terminal photolinker using carbodiimide chemistry (1-Ethyl-3-[3-dimethylaminopropyl] carbodiimide Hydrochloride; Pierce).

Example 3

Building A Library of Different Bead Constructs

Libraries of different bead constructs, for example with different coding moieties, are prepared by synthesizing a variety of different coding sequences, amino acids (20 amino acids) or PNAs (4 peptide nucleic acids) to beads utilizing photolinkers at the beginning and end of each sequence. The constructs are completed by attaching specific binding entities to each library pool.

Example 4

A Reaction And Measurement Scheme

1. A set of constructs from the library is assembled containing various binding entities for peptide analytes typically found in blood serum (angiotensin, bradykinin, glucofibrinopeptides, etc). For redundancy purposes, several replicate constructs are included. The total number of constructs may be approximately the number of analytes being measured (e.g. 20) times the redundancy number (e.g. 20).

2. The constructs are pooled and reacted with a small volume of serum at a buffered pH of approximately 7.0.
3. After the reaction time is complete, constructs are separated and washed from un-reacted serum components by centrifugation.
4. Constructs can be physically separated into individual reaction wells or placed onto MALDI-TOF sample targets. A small volume of MALDI matrix (5 mg/ml of 4-cyano-hydroxycinnamic acid in 1% trifluoroacetic acid) is added to the constructs on the sample target. After drying, the targets are placed into the instrument for analysis. The typical MALDI-TOF laser source (337-355 nm) has sufficient energy typically in a 100 nm beam diameter to cause photodissocation of the coding sequence, while the analyte:binding entity pair is dissociated due to the acidic environment. Both the coding sequence and the peptide analytes are ionized and enter the TOF for mass and intensity measurements.

Alternately, constructs can be dissociated by UV light and TFA solutions from individual wells can be aspirated into an electrospray source for analysis by mass spectrometry.

The invention claimed is:
1. A method for sample analysis comprising the steps of:
a) providing a composition comprising:
a solid support; and
a linked construct comprising:
a coding moiety; and
a binding moiety,
wherein the coding moiety is attached to the solid support through a first linker, the binding moiety is attached to the coding moiety through a second linker, and the binding moiety is capable of specifically binding an analyte;
b) contacting the composition with a sample to be tested for the absence, presence, or quantity of the analyte;
c) exposing the sample-contacted composition to conditions effectuating a release of at least one of the coding moiety, the binding moiety and the analyte from the solid support; and
d) subjecting at least one of the coding moiety and the analyte to spectrographic analysis.
2. The method of claim 1, wherein step d) comprises subjecting both the coding moiety and the analyte to spectrographic analysis.
3. The method of claim 1, wherein the spectrographic analysis comprises mass spectroscopy.
4. The method of claim 3, wherein mass spectroscopy is performed using MALDI-TOF, q-TOF, TOF-TOF, ICP, ESI, tandem, quadrupole, SIMS, or FAB mass spectroscopy.
5. The method of claim 4, wherein mass spectroscopy is ICP mass spectroscopy and the release of at least one of the coding moiety and the analyte is effectuated by plasma.
6. The method of claim 1, wherein the solid support is a chip.
7. The method of claim 1, wherein the solid support is a bead.
8. The method of claim 1, wherein the release of at least one of the coding moiety, the binding moiety and the analyte takes place in a mass spectrometer.
9. The method of claim 8, wherein releasing the coding moiety, the binding moiety or the analyte comprises using a MALDI matrix solution.
10. The method of claim 1, wherein the release the coding moiety, the binding moiety or the analyte comprises exposing the composition to a light source.
11. The method of claim 10, wherein the light source is a laser.
12. The method of claim 11, wherein the laser is a MALDI laser.
13. The method of claim 10, wherein the light source irradiates one bead at a time.

14. The method of claim 1, wherein spectrographic analysis of the coding moiety is used to identify the analyte.

15. The method of claim 14, wherein the spectrographic analysis of the coding moiety is used to quantify the amount of the analyte.

16. The method of claim 14, wherein the spectrographic analysis of the coding moiety is used to identify the source of the analyte.

17. The method of claim 1, further comprising the step of separating the beads before the step of exposing the sample-contacted composition to conditions effectuating a release of at least one of the coding moiety, the binding moiety, and the analyte from the solid support.

18. The method of claim 17, wherein the step of separating the beads comprises placing the beads in a micro-array of wells.

19. The method of claim 17, wherein the step of separating the beads comprises spreading the beads on a target.

20. The method of claim 19, wherein the target is a MALDI target.

21. The method of claim 1, wherein the coding moiety is analyzed by absorbance, fluorescence, IR spectroscopy, Raman spectroscopy, NMR spectroscopy, radioisotope detection, or radiofrequency detection.

22. A method for measuring binding affinity of an analyte comprising:
a) providing a composition comprising:
a solid support;
a linked construct comprising:
a coding moiety; and
a binding moiety; and
a first analyte,
wherein the coding moiety is attached to the solid support through a first linker, the binding moiety is attached to the coding moiety through a second linker, and the binding moiety is specifically bound to a first analyte;
b) contacting the composition of step a) with a sample containing a second analyte capable of specific binding to the binding moiety, wherein at least a portion of the first analyte is displaced by the second analyte;
c) exposing the sample-contacted composition to conditions effectuating release of the coding moiety and at least one of the first and the second analytes bound to the binding moiety from the solid support;
d) subjecting the coding moiety and at least one of the first and the second analytes to mass spectrographic analysis.

23. The method of claim 22, wherein the method is a competitive immunoassay.

24. The method of claim 22, wherein the composition of step a) comprises a plurality of linked constructs.

25. The method of claim 22, further comprising repeating steps a) to d) with a plurality of samples.

26. The method of claim 25, wherein each sample contains a different analyte.

27. The method of claim 26, further comprising the step of quantitating the amount of at least one of the first and the second analyte.

28. The method of claim 22, further comprising the step of determining a relative binding affinity for the binding moiety of the second analyte with respect to the first analyte.

29. The method of claim 22, wherein the first analyte and the second analyte are nucleic acids.

30. A method for measuring binding affinity of an analyte comprising:
a) providing a composition comprising:
a solid support;
a linked construct comprising:
a coding moiety; and
a binding moiety; and
a first analyte,
wherein the coding moiety is attached to the solid support through a first linker, the binding moiety is attached to the coding moiety through a second linker, and the binding moiety is bound to the first analyte;
b) contacting the composition of step a) with a sample containing a second analyte capable of binding to the first analyte, wherein the first analyte remains bound to the binding moiety;
c) exposing the sample-contacted composition to conditions effectuating release of the coding moiety and at least one of the first or the second analyte from the solid support;
d) subjecting the coding moiety and at least one of the first and the second analytes to spectrographic analysis.

31. The method of claim 30, wherein the binding moiety is an antibody, the first analyte is an antigen, and the second analyte is an antibody different from the binding moiety.

32. The method of claim 30, wherein the spectrographic analysis comprises mass spectroscopy.

33. A composition comprising:
a solid support; and
a linked construct comprising:
a coding moiety; and
a binding moiety,
wherein the coding moiety is attached to the solid support through a first linker, the binding moiety is attached to the coding moiety through a second linker, and the binding moiety is capable of specifically binding an analyte,
wherein the coding moiety consists of amino acids and
wherein the first linker and/or the second linker is selected from the group consisting of o-nitrobenzyl, alkyl derivative of o-nitrobenzyl, alkoxy derivative of o-nitrobenzyl, 7-nitroindanyl, 2-nitrobenzhydryl ester, 2-nitrobenzhydryl ether, n-alkylsulphonamide, 9-fluorenylmethyloxycarbonyl and oxime.

34. The composition of claim 33, wherein the first linker and/or the second linker is selected from the group consisting of o-nitrobenzyl, alkyl derivative of o-nitrobenzyl and alkoxy derivative of o-nitrobenzyl.

35. The composition of claim 33, wherein the first linker and/or the second linker is 7-nitroindanyl.

36. The composition of claim 33, wherein the first linker and/or the second linker is a 2-nitrobenzhydryl ester.

37. The composition of claim 33, wherein the first linker and/or the second linker is a 2-nitrobenzhydryl ether.

38. The composition of claim 33, wherein the first linker and/or the second linker is n-alkylsulphonamide.

39. The composition of claim 33, wherein the first linker and/or the second linker is 9-fluorenylmethyloxycarbonyl.

40. The composition of claim 33, wherein the first linker and/or the second linker is oxime.

41. The composition of claim 33, wherein the coding moiety comprises about 5-20 amino acids.

42. The composition of claim 33, wherein the binding moiety is selected from the group consisting of an antibody, an antigen, a protein, a peptide, a nucleic acid, a PNA, a carbohydrate, an antibody fragment, an antigen fragment, a protein fragment, a peptide fragment, a nucleic acid fragment, a PNA fragment, and a carbohydrate fragment.

* * * * *